United States Patent [19]

Harth et al.

[11] Patent Number: 4,587,059

[45] Date of Patent: May 6, 1986

[54] PROCESS FOR PRODUCTION OF 2-CYANOACRYLATES FROM 2,4-DICYANOGLUTARATES

[75] Inventors: Hubert Harth, Duesseldorf; Willi Wuest, Ratingen; Hans-Athanas Bruhn, Guenzburg; Miklos Danielisz, Hanover; Erbo Heinrich, Wennigsen, all of Fed. Rep. of Germany

[73] Assignee: Henkel Kommanditgesellschaft auf Aktien, Duesseldorf, Fed. Rep. of Germany

[21] Appl. No.: 596,753

[22] Filed: Apr. 4, 1984

[30] Foreign Application Priority Data

Apr. 7, 1983 [DE] Fed. Rep. of Germany ....... 3312427

[51] Int. Cl.$^4$ .................. C07C 120/00; C07C 121/30; C07C 121/48; C07C 121/60
[52] U.S. Cl. .................................... 558/400; 558/442
[58] Field of Search ................. 260/465.4, 464, 465 D

[56] References Cited

U.S. PATENT DOCUMENTS

| | | |
|---|---|---|
| 2,763,677 | 9/1956 | Jeremias ............................ 260/465.4 |
| 2,912,454 | 11/1959 | McKeever ......................... 260/465.4 |
| 2,926,188 | 2/1960 | McKeever et al. ............... 260/465.4 |
| 3,254,111 | 5/1966 | Hawkins et al. ................. 260/465.4 |
| 3,465,027 | 9/1969 | Hawkins ......................... 260/465.4 X |
| 3,577,394 | 5/1971 | Harrington .................. 260/465.4 X |
| 3,654,340 | 4/1972 | Banitt ............................... 260/465.4 |
| 4,328,170 | 5/1982 | Okawara et al. ............... 260/464 X |

FOREIGN PATENT DOCUMENTS 1258408  1/1968  Fed. Rep. of Germany .
3233007  3/1984  Fed. Rep. of Germany .

OTHER PUBLICATIONS

Hellmann et al., Chem. Berichte 90, (1957) pp. 535–536.

*Primary Examiner*—Joseph Paul Brust
*Attorney, Agent, or Firm*—Ernest G. Szoke; Henry E. Millson, Jr.; Mark A. Greenfield

[57] ABSTRACT

A process for preparing monomeric 2-cyanoacrylates by reacting a dicyanoglutarate with formaldehyde in the presence of water and under acid pH conditions, then removing the water and thermolyzing the intermediate reaction product.

8 Claims, No Drawings

PROCESS FOR PRODUCTION OF 2-CYANOACRYLATES FROM 2,4-DICYANOGLUTARATES

BACKGROUND OF THE INVENTION

1. Field of the Invention

This invention relates to monomeric adhesive materials and more particularly relates to a new process for producing monomeric 2-cyanoacrylates.

2. Description of the Prior Art 2,4-Dicyanoglutarates (symmetrical diesters of 2,4-dicyanoglutaric acid) are starting materials obtainable by reacting 2 moles of cyanoacetate with 1 mole of formaldehyde for the synthesis of 2-cyanoacrylates, although they are also formed as secondary products in the production of 2-cyanoacrylates. Numerous attempts have made to convert these valuable starting materials (whether specifically produced or obtained as residue in the thermolysis of oligomeric 2-cyanoacrylates in admixture with other substances) into 2-cyanoacrylates.

Thus, it was proposed in the U.S. Pat. No. 2,926,188 to split 2,4-dicyanoglutarates thermally into 2-cyanoacrylates and cyanoacetates. The process is carried out at temperatures in the range of from 175° C. to 210° C. Unfortunately, these high reaction temperatures promote secondary reactions to the detriment of the yield. Because of this, it was proposed in German Patent Application No. 32 33 007, first publicly disclosed on Mar. 8, 1984, to catalyze the thermolysis process by using bases, such as alkali or alkaline earth alcoholates. This makes it possible to carry out the reaction at temperatures in the range of from 90° C. to 130° C. and to obtain 2-cyanoacrylates in an increased yield. Since the boiling points of cyanoacetates and 2-cyanoacrylates differ only slightly in some cases, depending on the alcohol used for esterification, fairly complicated distillation systems have to be used in both processes mentioned above to enable the products to be obtained in the required purity.

In addition, it is known from U.S. Pat. No. 3,254,111 that 2,4-dicyanoglutarates can be condensed with paraformaldehyde in the presence of basic catalysts and that the product thus obtained can be thermally split into 2-cyanoacrylates. The disadvantage of this process lies in the relatively poor yields of 2-cyanoacrylate. If, in addition, an amine, for example piperidine, is used as the condensation catalyst, the products obtained have poor bonding properties. Furthermore, additional expense is involved in removing the benzene used as entraining agent.

Accordingly, there is a need for a new process for producing 2-cyanoacrylates from 2,4-dicyanoglutarates in high yields at relatively low temperatures. In addition, the products must have the purity required for bonding purposes.

DESCRIPTION OF THE INVENTION

The present invention provides a process for producing 2-cyanoacrylates from 2,4-dicyanoglutarates which satisfies the above requirements of high yields and purities at relatively low reaction temperatures. Also, the invention is directed to improving the yield in the production of 2-cyanoacrylates from cyanoacetates and formaldehyde or polyoxymethylene by improved recycling of the 2,4-dicyanoglutarates obtained as secondary reaction products.

Accordingly, the present invention relates to a process for the production of monomeric 2-cyanoacrylates by reacting 2,4-dicyanoglutarates with formaldehyde and/or polyoxymethylene, followed by thermolysis of the oligomers formed, wherein the reaction of the 2,4-dicyanoglutarates with formaldehyde and/or polyoxymethylene is carried out in the presence of water at an acid pH-value of from about 3 up to slightly less than 7.

In the production of monomeric 2-cyanoacrylates, it is standard practice to condense cyanoacetates or 2,4-dicyanoglutarates with formaldehyde and/or polyoxymethylene and to subject the resulting condensates to thermolysis after drying. In the present context, polyoxymethylenes are understood to be cyclic and linear polymers of formaldehyde, for example trioxane and/or paraformaldehyde. Hitherto, it was regarded as necessary to catalyze the condensation reaction with a basic catalyst. In addition, it was standard practice for the water of reaction formed from formaldehyde during the condensation reaction to be removed by entraining agents, such as benzene or xylene, during the reaction. The present invention breaks with these established concepts. Thus, the present condensation reaction is carried out in the presence of water and at an acid pH-value in the range of from about 3 up to slightly less than 7.

Insofar as the subsequent thermolysis step is concerned, the process of the invention gives the best results when the condensation reaction is carried out at an acid pH-value in the range of from about 3 to slightly less than 7 and preferably at a pH-value in the range of from about 4 to about 6. Numerous organic or inorganic acids can be added to obtain that pH-value. However, it is preferred to use nonvolatile acids or acid salts. Thus, acid salts of phosphoric acid or sulfuric acid are particularly suitable. In many cases, the 2,4-dicyanoglutarates used already contain carboxylic acid groups formed by hydrolysis so that suspensions of the starting products in water already have the pH-value required for the reaction. In some cases, the acid content is so high that partial neutralization has to be carried out to reach the required pH-range. Suitable neutralizing agents are nonvolatile neutralizing agents which are unlikely to form any secondary products under the thermolysis conditions. Thus, hydroxides of the alkali and alkaline earth metals are particularly suitable. It is also possible to use buffer mixtures active at acid pH-values of from about 3 to about 7, such as for example mixtures of hydrogen phosphates and dihydrogen phosphates.

In the practice of the process of the invention, it is important to utilize certain quantities of water. The quantity of water used should amount to between about 0.5 and about 5 moles of water per mole of 2,4-dicyanoglutarate and should not differ significantly from those values. Particularly favorable results are obtained when between about 0.8 and about 1.2 moles of water are used per mole of 2,4-dicyanoglutarate.

The 2,4-dicyanoglutarates are insoluble or only partially soluble in the quantities of water set forth above. Instead, dispersions having an emulsion-like appearance and—to the benefit of the process—a low viscosity are formed under the reaction conditions.

From about 0.5 to about 1 mole of formaldehyde and/or polyoxymethylene is used per mole of 2,4-dicyanoglutarate in the condensation step of the process of the invention. Formaldehyde can be used in the form of an aqueous solution. In one preferred embodiment, polyoxymethylene is used instead of formaldehyde. It is also possible to use mixtures, e.g., unstabilized formaldehyde solutions containing a certain percentage of polyoxymethylene, particularly paraformaldehyde. In every case, the preferred molar ratio amounts to between about 0.60 and about 0.85 mole of formaldehyde or formaldehyde derivative per mole of 2,4-dicyanoglutarate.

To carry out the process of the invention in a preferred manner, the 2,4-dicyanoglutarate is first mixed with water in a suitable reaction vessel, for example in a stirrer-equipped autoclave, resulting in the formation of an emulsion-like dispersion. The desired pH-range of about pH 3 to slightly less than 7 and preferably about pH 4-6 is then adjusted either with acids or, where acids are already present in the starting materials, with neutralizing agents. Formaldehyde and/or polyoxymethylene is then added. The reaction vessel is closed and heated to a temperature in the range of from about 70° C. to about 140° C. and preferably to a temperature in the range of from about 100° C. to about 130° C. An excess pressure thereby builds up. The reaction mixture is left standing under pressure at that temperature for between about 15 and about 60 minutes and preferably for between about 30 and about 45 minutes. The reaction vessel is then vented and the water added together with the water of reaction are removed by distillation from the condensation product formed.

The condensation product does not differ significantly from the condensation product of cyanoacetate and a substoichiometric quantity of formaldehyde which can be produced, for example, by known methods. After drying, which is preferably carried out at about 100° C. to about 120° C. in a steam jet vacuum or in an oil pump vacuum (pressure below 1 mbar), the products are split to form 2-cyanoacrylates. This can be done, for example, by the process of German Application No. 12 58 408. For example, thermolysis can conveniently be carried out by heating the products at a temperature in the range of from about 100° C. to about 185° C. for a period of time sufficient to effect the conversion, such as about 2 hours. To avoid polymerization of the 2-cyanoacrylates, gaseous $SO_2$ is passed through the thermolysis reaction mixture.

The 2,4-dicyanoglutarates used in the process of the invention have the following formula:

wherein RO and R'O can be the same or different, and are derived (by loss of a hydrogen atom) from $C_1$-$C_8$ straight or branched chain alkanols; cyclohexanol; phenyl substituted $C_1$-$C_8$ alkanols, such as benzyl alcohol; lower alkenols; mono $C_1$-$C_8$ alkyl ethers of ethylene glycol or propylene glycol; $C_9$-$C_{19}$ linear, branched, or cyclic monoalcohols or ether alcohols; or phenol.

The 2-cyanoacrylates produced by the process of the invention have the formulae:

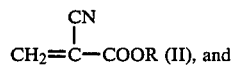

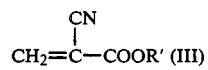

wherein RO and R'O in the above formulae have the meanings given above for the 2,4-dicyanoglutarates of Formula I.

2,4-dicyanoglutarates of different purity and also esters of 2,4-dicyanoglutaric acid with a variety of different alcohols can be used in the process of the invention. For example, it is possible to use chemically pure or almost pure 2,4-dicyanoglutarates which have been produced by the Hellmann and K. Stegmueller process described in Chem. Berichte 90, 535 (1957). However, it is preferred to use the 2-4-dicyanoglutarates accumulating as secondary products in the production of 2-cyanoacrylates. Secondary products such as these typically contain from about 50 to 85% by weight of 2,4-dicyanoglutarate. They can also contain oligomeric cyanoacrylates as well as secondary products.

Symmetrical esters of 2,4-dicyanoglutaric acid are preferably used for the process of the invention. These compounds are esters in which both carboxyl groups have been reacted with the same alcohol. Suitable esters are derived in particular from the following alcohols: methanol, ethanol, propanol, butanol, pentanol, hexanol and also isomers thereof, cyclohexanol, benzyl alcohol, allyl alcohol, monoethers of ethylene glycol or propylene glycol, 2-ethyl hexanol and also from linear, branched or cyclic monoalcohols or ether alcohols containing from 9 to 19 carbon atoms. In addition, the process of the invention is particularly suitable for phenol esters.

The advantages of the process of the invention lie in the increased yield of 2-cyanoacrylates by comparison with prior art methods; in the absence of organic solvents; in the low viscosity of the reaction medium, which requires only minimal stirring energy; and in the high purity of the 2-cyanoacrylates ultimately obtained.

The invention will be illustrated but not limited by the following examples.

EXAMPLES

EXAMPLE 1

102 kg (approximately 400 moles) of 2,4-dicyanoglutaric acid diethyl ester (approximately 94%) were mixed with 20 kg of water in a 400 liter capacity stirrer-equipped vessel, followed by the addition of 8.5 kg (261 moles) of polyoxymethylene (92%). To adjust to a pH-value of from 4 to 6, 383 g of a 32% NaOH solution (corresponding to 3.08 moles) were added. The reaction was carried out with stirring at a temperature of from 80° C. to 130° C. under the pressure spontaneously built up in the closed vessel. The reaction time was 45 minutes. The added water and the water of reaction were distilled off in a steam jet vacuum. The resulting condensation product was then subjected to thermolysis for 120 minutes at a temperature of from 150° C. to 180° C. under a pressure of less than 1 bar. To prevent polymerization, $SO_2$ gas was passed through the thermolysis reaction mixture and through the distillate in the following distillation step. Distillation of the crude product formed during thermolysis produced 48.6 kg (389 moles) of 2-cyanoacrylic acid ethyl ester. This yield was 51% by weight, based on the dicyanoglutarate used.

EXAMPLE 2

In a 400 liter capacity stirrer-equipped vessel, 130 kg of distillation residue from the production of 2-cyanoacrylate, containing 75.1% by weight of 2,4-dicyanoglutaric acid diethyl ester (410 moles), were mixed with 21.3 kg of water and the resulting mixture reacted with 8.83 kg of 92% polyoxymethylene (271 moles) in the presence of 804.6 g of 32% NaOH solution which was required to adjust the pH into the range of from 4 to 6. The reaction was carried out and the reaction product worked up in the same way as described in EXAMPLE 1. 58.7 kg of pure 2-cyanoacrylic acid ethyl ester were obtained, corresponding to a yield of 60.1% by weight, based on 100% 2,4-dicyanoglutarate.

The monomers produced in accordance with EXAMPLES 1 and 2 satisfy the quality requirements normally applied to reactive adhesives.

COMPARISON EXAMPLE 494.0 g (2.074 moles) of 2,4-dicyanoglutaric acid diethyl ester were reacted in the absence of water with 44.8 g of polyoxymethylene (92%; 1.372 moles) and 3 g of a 30% solution of sodium methylate in methanol (0.0167 mole). The quantity of sodium methylate used corresponded to an excess of 1.25 millimoles per mole of dicyanoglutarate. The reaction was carried out over a period of 45 minutes at a temperature of 100° C.–130° C. The water present was then removed using an oil pump vacuum. Thermolysis produced 154.5 g (1.236 moles) of 2-cyanoacrylic acid ethyl ester after distillation. The yield thus amounted to 31.3% by weight, based on 2,4-dicyanoglutarate.

What is claimed is:

1. A process for the preparation of monomeric 2-cyano-acrylates comprising the steps of
    (a) reacting (i) a 2,4-dicyanoglutarate of the formula

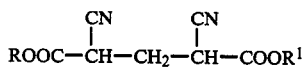 (I)

wherein RO and R$^1$O can be the same or different, and are derived from: $C_{1-8}$ linear or branched alkanols; cyclohexanol; phenyl substituted $C_{1-8}$ alkanols; lower alkenols; mono $C_{1-8}$ alkyl ethers of ethylene glycol or propylene glycol; $C_{9-19}$ linear unsubstituted, branched or cyclic monoalcohols or ether alcohols; or phenol; with
    (ii) formaldehyde, cyclic or linear polymers of formaldehyde, or a mixture thereof,
    in the presence of between about 0.5 and about 5 mols of water per mol of 2,4-dicyanoglutarate, at an acid pH of about 3 to slightly less than 7, and at a temperature of about 70° C. to about 140° C., to form an oligomeric intermediate product, and
    (b) removing water that is present from step (a) and thermolyzing said oligomeric intermediate product for a period of time sufficient to effect its conversion to monomeric 2-cyanoacrylates of the formulae

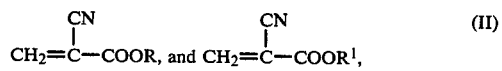 (II)

wherein RO and R$^1$O have the meanings given above.

2. A process in accordance with claim 1 wherein the step (a) reaction is carried out in the presence of at least one substantially nonvolatile inorganic acid or acid salt thereof.

3. A process in accordance with claim 1 wherein the 2,4-dicyanoglutarate of Formula I is the secondary reaction product from the synthesis of 2-cyanoacrylate and which contains from about 50 to about 95% by weight, based on the weight of said secondary reaction product, of 2,4-dicyanoglutarate.

4. A process in accordance with claim 1 wherein from about 0.8 to about 1.2 moles of water are present per mole of 2,4-dicyanoglutarate.

5. A process in accordance with claim 1 wherein from about 0.5 to about 1 mole of formaldehyde, cyclic or linear polymers of formaldehyde, or a mixture thereof is employed per mole of 2,4-dicyanoglutarate.

6. A process in accordance with claim 5 wherein from about 0.60 to about 0.85 mole is employed.

7. A process in accordance with claim 1 wherein step (a) is carried out under pressure in a closed reaction vessel.

8. A process in accordance with claim 7 wherein the temperature of step (a) is from about 100° C. to about 130° C.

* * * * *